United States Patent
Yoshihama et al.

[11] Patent Number: 6,080,781
[45] Date of Patent: Jun. 27, 2000

[54] TETRALONE OR BENZOPYRANONE DERIVATIVES AND A METHOD FOR PRODUCING THEM

[75] Inventors: Makoto Yoshihama; Masamichi Nakakoshi; Junji Nakamura; Shoji Nakayama, all of Tochigi, Japan

[73] Assignee: Snow Brand Milk Products Co., Ltd., Hokkaido, Japan

[21] Appl. No.: 09/155,513

[22] PCT Filed: Jan. 28, 1998

[86] PCT No.: PCT/JP98/00344

§ 371 Date: Jan. 19, 1999

§ 102(e) Date: Jan. 19, 1999

[87] PCT Pub. No.: WO98/32724

PCT Pub. Date: Jul. 30, 1998

[30] Foreign Application Priority Data

Jan. 29, 1997 [JP] Japan ................................. 9-028258
Aug. 8, 1997 [JP] Japan ................................. 9-225564

[51] Int. Cl.[7] ................ A61K 31/352; A61K 31/122; C07D 311/22; C07C 49/643; C07C 49/697
[52] U.S. Cl. .................. 514/456; 514/681; 549/401; 568/327
[58] Field of Search ............... 549/401; 568/327; 514/456, 681

[56] References Cited

U.S. PATENT DOCUMENTS 3,833,726  9/1974  Schwender et al. ............ 568/327 X
3,843,665  10/1974 Coombs et al. ................ 568/327 X

FOREIGN PATENT DOCUMENTS 48-26155  5/1973  Japan .
1-157969  6/1989  Japan .
6-1784    1/1994  Japan .

OTHER PUBLICATIONS

Jain et al., Chemical Abstracts, 107:23130, 1987.
El–Kerdawy et al., Chemical Abstracts, 112:198081, 1990.
Boehler et al., Chemical Abstracts, 68:95625y, 1968.
Donnelly et al., Chemical Abstracts, 68:95626z, 1968.
Boehler, et al., *Chemical Abstracts*, 68:95625y (1968).
Donnelly, et al., *Chemical Abstracts*, 68:95626z (1968).

*Primary Examiner*—Fiona T. Powers
*Attorney, Agent, or Firm*—Townsend and Townsend and Crew LLP

[57] ABSTRACT

The present invention provides new tetralone or benzopyranone derivatives and a method for producing the derivatives useful for a therapeutic agent for preventing and/or treating hormone dependent diseases.

The present invention is a new tetralone or benzopyranone derivative represented by a particular general formula (I).

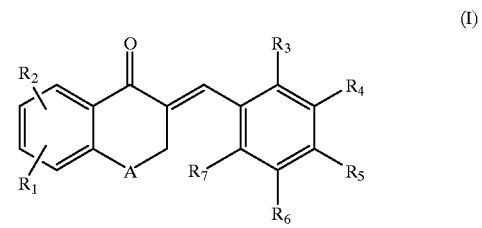

(I)

wherein $R_1$ and $R_2$ represent hydrogen, a hydroxy group, an alkyloxy group or an aralkyloxy group, respectively, $R_3$–$R_7$ represent hydrogen, a hydroxy group or a straight or branched alkyl, alkyloxy or aralkyloxy group having 1–6 carbon atoms, a halogen, an amino group or an alkylene dioxy group joined at $R_3$ and $R_4$, $R_4$ and $R_5$, $R_5$ and $R_6$, or $R_6$ and $R_7$, respectively, and A represents a methylene or oxygen.

In the production, a particular tetralone or benzopyranone compound and a particular benzaldehyde compound are reacted.

8 Claims, 3 Drawing Sheets

Fig. 1

| Example | Structural formula | molecular formula | molecular weight | 17β-HSD inhibition activity (%) *1 |
|---|---|---|---|---|
| 1 | | $C_{17}H_{14}O_4$ | 282.297 | 50.2±3.7 |
| 2 | | $C_{17}H_{14}O_2$ | 250.299 | 43.6±3.0 |
| 3 | | $C_{17}H_{14}O_3$ | 266.298 | 17.9±2.1 |
| 4 | | $C_{17}H_{14}O_3$ | 266.298 | 16.0±1.7 |
| 5 | | $C_{19}H_{16}O_5$ | 324.335 | 6.2±1.1 |
| 6 | | $C_{19}H_{19}NO_2$ | 293.367 | 4.1±1.9 |
| 7 | | $C_{19}H_{18}O_4$ | 310.351 | 7.2±0.3 |
| 8 | | $C_{19}H_{18}O_4$ | 310.351 | 3.6±0.3 |
| 9 | | $C_{17}H_{13}BrO_2$ | 329.195 | 7.3±1.4 |
| 10 | | $C_{17}H_{13}ClO_2$ | 284.743 | 8.6±1.9 |

*1: mean ± standard deviation

Fig. 2

| Example | Structural formula | molecular formula | molecular weight | 17β-HSD inhibition activity (%) *1 |
|---|---|---|---|---|
| 11 | | $C_{17}H_{13}FO_2$ | 268.289 | 8.6±2.1 |
| 12 | | $C_{18}H_{14}O_4$ | 294.309 | 15.4±4.3 |
| 13 | | $C_{19}H_{16}O_4$ | 308.336 | 13.9±1.7 |
| 14 | | $C_{16}H_{12}O_5$ | 284.270 | 57.9±5.3 |
| 15 | | $C_{17}H_{12}O_5$ | 296.281 | 31.1±4.1 |
| 16 | | $C_{18}H_{14}O_5$ | 310.308 | 29.2±2.5 |
| 17 | | $C_{18}H_{16}O_5$ | 312.324 | 30.2±1.9 |
| 18 | | $C_{19}H_{18}O_5$ | 326.351 | 25.4±3.9 |
| 19 | | $C_{19}H_{18}O_5$ | 326.351 | 32.9±5.7 |
| 20 | | $C_{20}H_{20}O_5$ | 340.378 | 28.1±2.3 |

*1; mean ± standard deviation

Fig. 3

| Example | Structural formula | molecular formula | molecular weight | 17β-HSO inhibition activity (%) *1 |
|---|---|---|---|---|
| 21 | (structure with HO-, O, CH₃, OCH₃ groups) | $C_{18}H_{18}O_5$ | 296.324 | 50.2±7.2 |
| 22 | (structure with H₃CO-, O, OCH₃, OCH₂CH₃ groups) | $C_{21}H_{22}O_4$ | 338.405 | — |

*1; mean ± standard deviation

TETRALONE OR BENZOPYRANONE DERIVATIVES AND A METHOD FOR PRODUCING THEM

TECHNICAL FIELD

The present invention relates to new tetralone or benzopyranone derivatives and a method for producing the derivatives. The new tetralone or benzopyranone derivatives of the present invention have inhibition activity of 17β-hydroxysteroid dehydrogenase (abbreviated as 17β-HSD, hereinafter), and these derivatives are useful for a therapeutic agent for preventing and/or treating androgen or estrogen dependent diseases, particularly, prostatic cancer, benign prostatic hyperplasia, virilism, mammary cancer, mastopathy, endometrial cancer, endometriosis, ovarian cancer and the like.

BACKGROUND ART

Lately, in our country, it causes trouble that androgen dependent diseases such as prostatic cancer and benign prostatic hyperplasia, and estrogen dependent diseases such as mammary cancer and endometriosis, are increasing in the morbidity. For example, the percentage of mortality of the prostatic cancer was 3.9 men per 100,000 of population by statistical data in 1984, and was about 1/10 of the non Caucasian men in the western country. However, it is increasing gradually by prolonging people's life due to improvement of medical treatment and western diet. In 1993, that percentage is 6.7 men per 100,000 of population and it is coming to European and U.S. levels. It is expected that the numbers of mortality based on the prostatic cancer in 2015 will be four times more of those in 1990. This is the worst increasing percentage in all cancers.

It has become clear from many views that subjective conditions and objective conditions of the androgen dependent diseases will be improved by depressing the androgen levels in blood. Therefore, treatment of these diseases have been accomplished by lowering the androgen in blood by castration, by administering an agonist of LH-RH to lower the androgen in blood to the castration level, and by administering anti-androgen agents antagonizing an androgen receptor to control the action of the androgen. In fact, the clinical effects are broadly noticed. However, since the castration causes a lowering of QOL, it is only proceeded in very limited diseases. The agonist of LH-RH has problems; side effect such as a bone pain or dysuria caused by a phenomenon peculiar to the agonist (temporary increase of the androgen), and rekindling for continuous existence of androgen originated from adrenal glands. Further, it is indicated that the effect of the anti-androgen agents is decreased by the development of variants of the androgen receptor during the medicine is administered. Therefore, "a method of complete blockage of the androgen" is prescribed for more effective endocrine treatment. The method is aimed to completely inhibit the androgen in blood by combination of several endocrine therapeutics, and more effective treatment is expected.

Testosterone exhibiting the most effective androgenic activity in $C_{19}$ steroids having androgenic activity can be biosynthesized with 17β-HSD from a substrate of andorostendione. By inhibiting this 17β-HSD, the concentration of testosterone in blood is directly lowered, so that it is expected to effectively treat the above androgen dependent diseases. In addition, since this enzyme is also a biosynthetic enzyme of estoradiol having the highest estrogenic activity in $C_{18}$ steroid having estrogenic activity, it is also expected to effectively treat the estrogen dependent diseases such as mammary cancer and endometriosis.

Steroid compounds and non-steroid compounds have been proposed as 17β-HSD inhibitors. As the non-steroid compounds, for example, flavons and isoflavons, which are described in Biochemical and Biophysical Research Communications, Vol. 215, 1137–1144 (1995), and fatty acids, which are described in Journal of Steroid Biochemistry, Vol. 23, 357–363 (1985), are known. However, since the activity of these compounds is not satisfied, it is expected to obtain materials having higher activity.

DISCLOSURE OF INVENTION

Considering the above problems, the inventors of the present invention earnestly have studied and found that new tetralone or benzopyranone derivatives have an excellent inhibition activity of 17β-HSD. Therefore, the present invention aims to provide the new tetralone or benzopyranone derivatives and a method for producing the derivatives.

The present invention relates to new tetralone or benzopyranone derivatives and a method for producing the derivatives. The new tetralone or benzopyranone derivatives of the present invention have inhibition activity of 17β-hydroxysteroid dehydrogenase (abbreviated as 17β-HSD, hereinafter), and these derivatives are useful for a therapeutic agent for preventing and/or treating androgen or estrogen dependent diseases, particularly, prostatic cancer, benign prostatic hyperplasia, virilism, mammary cancer, mastopathy, endometrial cancer, endometriosis, ovarian cancer and the like.

The derivatives of the present invention is a new tetralone or benzopyranone derivative represented by the following general formula (I):

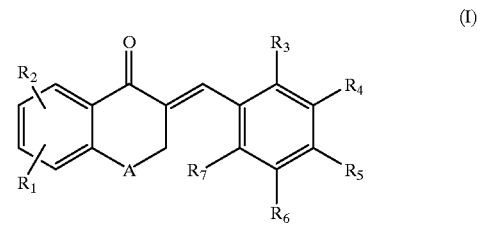

wherein $R_1$ and $R_2$ represent hydrogen, a hydroxy group, an alkyloxy group or an aralkyloxy group, respectively, $R_3$–$R_7$ represent hydrogen, a hydroxy group, or a straight or branched alkyl, alkyloxy or aralkyloxy group having 1–6 carbon atoms, a halogen, an amino group or an alkylene dioxy group joined at $R_3$ and $R_4$, $R_4$ and $R_5$, $R_5$ and $R_6$, or $R_6$ and $R_7$, respectively, and A represents a methylene or oxygen.

In addition, the present invention is characterized in that, for producing the new tetralone or benzopyranone derivatives, a tetralone or benzopyranone compound represented by the following general formula (II) and a benzaldehyde compound represented by the following general formula (III) are dissolved in an organic solvent and refluxed with heating or reacted under acidic conditions, and the reacted solution is purified.

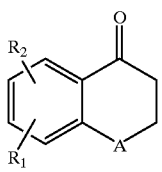

(II)

wherein $R_1$ and $R_2$ represent hydrogen, a hydroxy group, an alkyloxy or aralkyloxy group, respectively, and A represents a methylene or oxygen.

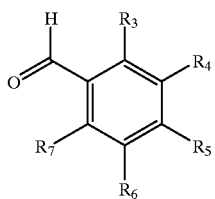

(III)

wherein $R_3$–$R_7$ represent hydrogen, a hydroxy group, or a straight or branched alkyl, alkyloxy or aralkyloxy group having 1–6 carbon atoms, a halogen, an amino group, or an alkylene dioxy group joined at $R_3$ and $R_4$, $R_4$ and $R_5$, $R_5$ and $R_6$, or $R_6$ and $R_7$, respectively.

As embodiments of new tetralone or benzopyranone derivatives represented by the following general formula (I), the following compounds can be exemplified. (The numbers of compounds and examples described in FIGS. 1–3 are coincident.)

(1) 2-[(3,4-dihydroxyphenyl)methylene]-6-hydroxy-1-tetralone
(2) 2-(phenylmethylene)-6-hydroxy-1-tetralone
(3) 2-[(3-hydroxyphenyl)methylene]-6-hydroxy-1-tetralone
(4) 2-[(4-hydroxyphenyl)methylene]-6-hydroxy-1 tetralone
(5) 2-[(2-methoxyphenyl-4-carboxylic acid)methylene]-6-hydroxy-1-tetralone
(6) 2-[(4-dimethylaminophenyl)methylene]-6-hydroxy-1-tetralone
(7) 2-[(3,4-dimethoxyphenyl)methylene]-6-hydroxy-1-tetralone
(8) 2-[(3,5-dimethoxyphenyl)methylene]-6-hydroxy-1-tetralone
(9) 2-[(4-bromophenyl)methylene]-6-hydroxy-1-tetralone
(10) 2-[(4-chlorophenyl)methylene]-6-hydroxy-1-tetralone
(11) 2-[(4-fluorophenyl)methylene]-6-hydroxy-1-tetralone
(12) 6-hydroxy-2-piperonylidene-1-tetralone
(13) 2-[(3,4-benzodioxane)-6-methylene]-6-hydroxy-1-tetralone
(14) 2-[(3,4-dihydroxyphenyl)methylene]-7-hydroxy-4(4H)-benzopyranone
(15) 7-hydroxy-3-piperonylidene-4-(4H)-benzopyranone
(16) 3-[(1,4-benzodioxane)-6-methylene]-7-hydroxy-4(4H)-benzopyranone
(17) 3-[(3,4-dimethoxyphenyl)methylene]-7-hydroxy-4(4H)-benzopyranone
(18) 3-[(3-ethoxy-4-methoxyphenyl)methylene]-7-hydroxy-4(4H)-benzopyranone
(19) 3-[(3-methoxy-4-ethoxyphenyl)methylene]-7-hydroxy-4(4H)-benzopyranone
(20) 3-[(3,4-diethoxyphenyl)methylene]-7-hydroxy-4(4H)-benzopyranone
(21) 3-[(3-methyl-4-methoxyphenyl)methylene]-7-hydroxy-4(4H)-benzopyranone
(22) 2-methoxy[(3-methoxy-4-ethoxyphenyl)methylene]-6-methoxy-1-tetralone The derivatives of the present invention contain, in addition to the above-mentioned compounds, stereospecific isomers of these compounds, and salts formed with acids or bases. As the salts of bases, for example, salts of inorganic bases of sodium, potassium, magnesium, calcium or aluminum, salts of organic bases of lower alkyl amines or lower alcohol amines, salts of basic amino acids such as lysine, alginine, or ornithine, or ammonium salts are exemplified. Further, the derivatives may form hydrates, solvates of lower alcohols, and crystal polymorphs.

The derivatives of the present invention can be prepared by the following methods. As an example, above-mentioned tetralone or benzopyranone compounds (II) and above-mentioned benzaldehyde compounds (III) are dissolved in solvent such as methanol, ethanol or propanol, concentrated hydrochloric acid is added, the solution is refluxed with heating for 1–24 hours and cooled, precipitated crystals are filtered to obtain desired new derivatives of the present invention (I). When crystals are not precipitated, water 100–400 ml is added to precipitate crystals, and the crystals are filtered and dried to obtain the desired derivatives of the present invention. Otherwise, sodium hydroxide or potassium hydroxide is added to compounds (II) and (III) in solvent such as methanol, ethanol or propanol, the solution is stirred for 1–24 hours and acidified with hydrochloric acid, and precipitated crystals are filtered to obtain the desired derivatives of the present invention. In addition, the desired derivatives of the present invention can be obtained by dissolving the above compounds in a hydrochloric gas-saturated solution of organic solvent such as methanol, ethanol, propanol or ether; then cooling, allowing to stand at room temperature or heating the solution; stirring for 1–24 hours; adding water to precipitate the desired derivatives as crystals; and filtering the precipitated crystals.

The derivatives of the present invention can safely be orally or parenterally administered as medicines to man or animals. In the case of parenteral administration, intravenous injection, intramuscular injection, subcutaneous injection, intra-abdominal injection, percutaneous administration, administration through the lungs, intranasal injection, administration through the intestines, administration from oral cavity, and administration through mucosae can be exemplified, and these medicines are administered. Injections, suppository, aerosols and percutaneous absorption tapes and the like can be exemplified. As the medicines of oral administration, tablets (including sugar-coated tablets, coating tablets and buccal tablets), powder, capsules (including a soft capsule), granules (including a coating granule), pills, troches, liquid preparations, or sustained release preparations of these medicines, which are pharmaceutically allowable, can be exemplified. As the liquid for oral administration, suspension, emulsion, syrup (including dry syrup), and elixir can be exemplified. These pharmaceuticals are prepared by conventional methods of manufacturing pharmacy and administered as drug compositions along with pharmacologically allowable carriers, vehicles, disintegrators, lubricants, coloring matters and the like.

As the carriers and vehicles used in these pharmaceuticals, lactose, glucose, sucrose, mannitol, potato starch, corn starch, calcium carbonate, calcium phosphate, calcium sulfate, crystalline cellulose, powdered glycyrrhiza, and powdered gentian can be exemplified. As the binders, starch, tragacanth gum, gelatin, syrup, polyvinylalcohol, polyvinylether, polyvinylpyrrolidone, hydroxypropylcellulose, methylcellulose, ethylcellulose, and carboxymethylcellulose can be exemplified. As the disintegrators, starch, agar, powdered gelatin, sodium carboxymethylcellulose, calcium carboxymethylcellulose, crystalline cellulose, calcium carbonate, calcium bicarbonate, and sodium alginic acid can be exemplified. As the lubricants, magnesium stearate, talc, hydrogenated vegetable oil, and macrogol can be exemplified. As the coloring matters, matters which are allowed to add to medicines can be used.

The tablets and granules can be coated with sucrose, gelatin, hydroxypropylcellulose, purified shellac, gelatin, glycerin, sorbitol, ethylcellulose, hydroxypropylcellulose, hydroxypropylmethylcellulose, polyvinylpyrrolidone, phthalic acid cellulose acetate, hydroxypropylmethylcellulose phthalate, methylmethacrylate, methacryic acid polymer or the like, and one or more coatings may be used. Capsules of ethylcellulose or gelatin may be used. Further, when the injections are prepared, if necessary, a pH adjustor, a buffering agent, a stabilizer, a solubilizing agent or the like may be added to the basis by a conventional method.

When the derivatives of the present invention are administered to patients, the dose is not particularly limited because conditions such as the condition of illness, and patient's age, health condition and weight are different, it is about 1 mg–1,000 mg per day for an adult, preferably 50–200 mg, orally or parenterally one time or more a day.

Further, the derivatives of the present invention, in the production of semiconductor devices and the like, can be used in a photoresist composition of a positive type, which gives high sensitive resolution, development properties, heat-resisting properties, and resist patterns having excellent resist forms.

BRIEF DESCRIPTION OF THE DRAWINGS

[FIG. 1] A drawing, which shows the results of examples.
[FIG. 2] A drawing, which shows the results of examples.
[FIG. 3] A drawing, which shows the results of examples.

BEST MODE FOR CARRYING OUT THE INVENTION

The following Examples are intended to further illustrate the present invention and not to limit the invention by these Examples.

EXAMPLE 1

Synthesis of 2-[(3,4-dihydroxyphenyl)methylene]-6-hydroxy-1-tetralone

After 6-hydroxy-1-tetralone 1.0 g and 3,4-dihydroxybenzaldehyde 0.85 g were added to a mixture of concentrated hydrochloric acid 50 ml and methanol 75 ml, the mixture was refluxed for 2.5 hours and cooled to room temperature, and water 357 ml was added. The precipitated crystals were filtered. The crystals were dried over phosphorous pentoxide for six hours under reduced pressure to obtain the desired compound 1.25 g.

FAB MASS (M+1); 283
$^1$H-NMR (ppm, in DMSO-$d_6$); 2.83 (2H, m), 3.02 (2H, m), 6.66 (1H, d, J=2.1 Hz), 6.75 (1H, dd, J=8.5, 2.4 Hz), 6.79 (1H, d, J=7.9 Hz), 6.83 (1H, dd, J=8.3, 1.9 Hz), 6.94 (1H, d, J=1.8 Hz), 7.49 (1H, s), 7.81 (1H, d, J=8.5 Hz), 9.09 (1H, s), 9.35 (1H, s), 10.31 (1H, s)

EXAMPLE 2

Synthesis of 2-(phenylmethylene)-6-hydroxy-1-tetralone

After 6-hydroxy-1-tetralone 1.0 g and benzaldehyde 0.42 ml were added to a mixture of concentrated hydrochloric acid 50 ml and methanol 75 ml, the mixture was refluxed for two hours and cooled to room temperature, and water 400 ml was added. The precipitated crystals were filtered. The crystals were dried over phosphorous pentoxide for six hours under reduced pressure to obtain the desired compound 0.756 g.

FAB MASS (M+1); 251
$^1$H-NMR (ppm, in DMSO-$d_6$); 2.83 (2H, m), 3.02 (2H, m), 6.66 (1H, s), 6.76 (1H, d, J=8.6 Hz), 7.44 (4H, m), 7.62 (1H, s), 7.84 (1H, d, J=8.8 Hz), 10.37 (1H, s)

EXAMPLE 3

Synthesis of 2-[(3-hydroxyphenyl)methylene]-6-hydroxy-1-tetralone

After 6-hydroxy-1-tetralone 1.0 g and 3-hydroxybenzaldehyde 0.903 g were added to a mixture of concentrated hydrochloric acid 50 ml and methanol 75 ml, the mixture was refluxed for one hour and cooled to room temperature, and water 400 ml was added. The precipitated crystals were filtered. The crystals were dried over phosphorous pentoxide for six hours under reduced pressure to obtain the desired compound 0.92 g.

FAB MASS (M+1); 267
$^1$H-NMR (ppm, in DMSO-$d_6$); 2.83 (2H, m), 2.99 (2H, m), 6.66 (1H, d, J=2.4 Hz), 6.76 (2H, m), 6.98 (2H, m), 7.23 (1H, t, J=7.0 Hz), 7.53 (1H, s), 7.84 (1H, d, J=8.4 Hz), 9.54 (1H, s), 10.39 (1H, s)

EXAMPLE 4

Synthesis of 2-[(4-hydroxyphenyl)methylene]-6-hydroxy-1-tetralone

After 6-hydroxy-1-tetralone 1.0 g and 4-hydroxybenzaldehyde 0.903 g were added to a mixture of concentrated hydrochloric acid 50 ml and methanol 75 ml, the mixture was refluxed for one hour and cooled to room temperature, and water 200 ml was added and allowed to stand for one hour. The precipitated crystals were filtered. The crystals were dried over phosphorous pentoxide for four hours under reduced pressure to obtain the desired compound 0.941 g.

FAB MASS (M+1); 267
$^1$H-NMR (ppm, in DMSO-$d_6$); 2.81 (2H, m), 3.00 (2H, m), 6.65 (1H, d, J=2.4 Hz), 6.75 (1H, dd, J=8.5, 2.1 Hz), 6.84 (2H, d, J=8.5 Hz), 7.35 (1H, d, J=8.8 Hz), 7.55 (1H, s), 7.82 (1H, d, J=8.5 Hz), 9.84 (1H, s), 10.33 (1H, s)

EXAMPLE 5

Synthesis of 2-[(2-methoxyphenyl-4-carboxylic acid)methylene]-6-hydroxy-1-tetralone After 6-hydroxy-1-tetralone 1.0 g and 4-formyl-2-methoxyphenyl acetate 1.44 g were added to a mixture of concentrated hydrochloric acid 50 ml and methanol 75 ml, the mixture was refluxed for one hour and cooled to room temperature, and water 400 ml was added and allowed to stand for two hours. The precipitated crystals were filtered. The crystals were dried over phosphorous pentoxide for four hours under reduced pressure to obtain the desired compound 0.671 g.

FAB MASS (M+1); 325
$^1$H-NMR (ppm, in DMSO-$d_6$); 2.82 (2H, m), 3.05 (2H, m), 3.81 (3H, s), 6.66 (1H, d, J=2.1 Hz), 6.75 (1H, dd, J=8.2, 2.1 Hz), 6.85 (1H, d, J=7.9 Hz), 6.98 (1H, dd, J=8.2, 1.8 Hz), 7.07 (1H, d, J=1.8 Hz), 7.58 (1H, s), 7.83 (1H, d, J=8.5 Hz)

EXAMPLE 6

Synthesis of 2-[(4-dimethylaminophenyl)methylene]-6-hydroxy-1-tetralone

After 6-hydroxy-1-tetralone 1.0 g and 4-dimethylaminobenzaldehyde 0.97 g were added to a mixture of concentrated hydrochloric acid 50 ml and methanol 75 ml, the mixture was refluxed for 1.5 hours and cooled to room temperature, and water 400 ml was added. The precipitated crystals were filtered. The crystals were dried over phosphorous pentoxide for six hours under reduced pressure to obtain the desired compound 0.885 g.

FAB MASS (M+1); 294

$^1$H-NMR (ppm, in DMSO-d$_6$); 2.81 (2H, m), 2.98 (6H, s), 3.03 (2H, m), 6.66 (1H, d, J=2.5 Hz), 6.75 (1H, dd, J=8.5, 2.4 Hz), 6.83 (1H, d, J=8.8 Hz), 7.40 (1H, d, J=8.8 Hz), 7.58 (1H, s), 7.82 (1H, d, J=8.5 Hz)

EXAMPLE 7

Synthesis of 2-[(3,4-dimethoxyphenyl)methylene]-6-hydroxy-1-tetralone

After 6-hydroxy-1-tetralone 1.0 g and 3,4-dimethoxybenzaldehyde 1.23 g were added to a mixture of concentrated hydrochloric acid 50 ml and methanol 75 ml, the mixture was refluxed for 1.5 hours and cooled to room temperature, and the precipitated crystals were filtered. The crystals were dried over phosphorous pentoxide for 5.5 hours under reduced pressure to obtain the desired compound 1.60 g.

FAB MASS (M+1); 311

$^1$H-NMR (ppm, in DMSO-d$_6$); 2.82 (2H, m), 3.06 (2H, m), 3.80 (6H, s), 6.66 (1H, d, J=2.1 Hz), 6.76 (1H, dd, J=8.5, 2.4 Hz), 7.01 (1H, d, J=8.8 Hz), 7.07 (2H, m), 7.60 (1H, s), 7.84 (1H, d, J=8.5 Hz), 10.19 (1H, s)

EXAMPLE 8

Synthesis of 2-[(3,5-dimethoxyphenyl)methylene]-6-hydroxy-1-tetralone

After 6-hydroxy-1-tetralone 1.0 g and 3,5-dimethoxybenzaldehyde 1.23 g were added to a mixture of concentrated hydrochloric acid 50 ml and methanol 75 ml, the mixture was refluxed for 1.5 hours and cooled to room temperature, and the precipitated crystals were filtered. The crystals were dried over phosphorous pentoxide for four hours under reduced pressure to obtain the desired compound 1.276 g.

FAB MASS (M+1); 311

$^1$H-NMR (ppm, in DMSO-d$_6$); 2.82 (2H, m), 2.93 (2H, s), 3.83 (3H, s), 3.87 (3H, s), 6.57 (1H, dd, J=8.2, 2.1 Hz), 6.63 (1H, dd, J=8.6, 2.1 Hz), 6.77 (1H, dd, J=8.5, 2.4 Hz), 7.29 (1H, d, J=8.5 Hz), 7.83 (1H, s), 7.84 (1H, d, J=8.5 Hz)

EXAMPLE 9

Synthesis of 2-[(4-bromophenyl)methylene]-6-hydroxy-1-tetralone

After 6-hydroxy-1-tetralone 1.0 g and 4-bromobenzaldehyde 1.37 g were added to a mixture of concentrated hydrochloric acid 50 ml and methanol 75 ml, the mixture was refluxed for one hour and cooled to room temperature, and water 250 ml was added. The precipitated crystals were filtered. The crystals were dried over phosphorous pentoxide for four hours under reduced pressure to obtain the desired compound 0.72 g.

FAB MASS (M+1); 330

$^1$H-NMR (ppm, in DMSO-d$_6$); 2.82 (2H, m), 2.97 (2H, m), 6.66 (1H, d, J=1.5 Hz), 6.77 (1H, dd, J=8.5, 2.4 Hz), 7.43 (2H, d, J=8.5 Hz), 7.56 (1H, s), 7.61 (2H, d, J=8.5 Hz), 7.85 (1H, d, J=8.5 Hz), 10.42 (1H, s)

EXAMPLE 10

Synthesis of 2-[(4-chlorophenyl)methylene]-6-hydroxy-1-tetralone

After 6-hydroxy-1-tetralone 1.0 g and 4-chlorobenzaldehyde 1.03 g were added to a mixture of concentrated hydrochloric acid 50 ml and methanol 75 ml, the mixture was refluxed for 1.5 hours and cooled to room temperature, and water 250 ml was added. The precipitated crystals were filtered. The crystals were dried over phosphorous pentoxide for four hours under reduced pressure to obtain the desired compound 0.77 g.

FAB MASS (M+1); 285

$^1$H-NMR (ppm, in DMSO-d$_6$); 2.82 (2H, m), 2.98 (2H, m), 6.66 (1H, d, J=2.1 Hz), 6.77 (1H, dd, J=8.5, 2.2 Hz), 7.48 (5H, m), 7.59 (1H, s), 7.85 (1H, d, J=8.5 Hz), 10.41 (1H, s)

EXAMPLE 11

Synthesis of 2-[(4-fluorophenyl)methylene]-6-hydroxy-1-tetralone

After 6-hydroxy-1-tetralone 1.0 g and 4-fluorobenzaldehyde 0.79 ml were added to a mixture of concentrated hydrochloric acid 50 ml and methanol 75 ml, the mixture was refluxed for 1.5 hours and cooled to room temperature, and water 300 mg was added. The precipitated crystals were filtered. The crystals were dried over phosphorous pentoxide for four hours under reduced pressure to obtain the desired compound 0.65 g.

FAB MASS (M+1); 269

$^1$H-NMR (ppm, in DMSO-d$_6$); 2.81 (2H, m), 2.98 (2H, m), 6.66 (1H, d, J=2.2 Hz), 6.77 (1H, dd, J=8.5, 2.5 Hz), 7.25 (2H, m), 7.53 (2H, m), 7.61 (1H, s), 7.84 (111, d, 15 J=8.5 Hz), 10.41 (1H, s)

EXAMPLE 12

Synthesis of 6-hydroxy-2-piperonylidene-1-tetralone

After 6-hydroxy-1-tetralone 1.0 g and piperonal 1.11 g were added to a mixture of concentrated hydrochloric acid 50 ml and methanol 75 ml, the mixture was refluxed for 0.5 hours and cooled to room temperature, and the precipitated crystals were filtered. The crystals were dried over phosphorous pentoxide for four hours under reduced pressure to obtain the desired compound 1.63 g.

FAB MASS (M+1); 295

$^1$H-NMR (ppm, in DMSO-d$_6$); 2.82 (2H, m), 3.01 (2H, m), 6.06 (2H, s), 6.65 (1H, d, J=2.1 Hz), 6.75 (1H, dd, J=8.5, 2.4 Hz), 6.98 (1H, d, J=7.9 Hz), 7.02 (1H, dd, J=9.4, 1.1 Hz), 7.08 (1H, d, J=1.5 Hz), 7.55 (1H, s), 7.82 (1H, d, J=8.5 Hz), 10.37 (1 H, s)

EXAMPLE 13

Synthesis of 2-[(3,4-benzodioxane)-6-methylene]-6-hydroxy-1-tetralone

After 6-hydroxy-1-tetralone 1.0 g and 1,4-benzodioxane-6-carbaldehyde 1.21 g were added to a mixture of concentrated hydrochloric acid 50 ml and methanol 75 ml, the mixture was refluxed for one hour and cooled to room temperature, and the precipitated crystals were filtered. The crystals were dried over phosphorous pentoxide for four hours under reduced pressure to obtain the desired compound 1.57 g.

FAB MASS (M+1); 309

$^1$H-NMR (ppm, in DMSO-d$_6$); 2.81 (2H, m), 3.00 (2H, m), 4.26 (4H, m), 6.65 (1H, d, J=2.4 Hz), 6.75 (1H, dd, J=8.5, 2.1 Hz), 6.90 (1H, d, J=8.2 Hz), 6.98 (1H, dd, J=8.5, 1.8 Hz), 7.01 (1H, d, J=2.1 Hz), 7.52 (1H, s), 7.82 (1H, d, J=8.6 Hz), 10.36 (1H, s)

EXAMPLE 14

Synthesis of 2-[(3,4-dihydroxyphenyl)methylene]-7-hydroxy-4(4H)-benzopyranone

After 7-hydroxy-4(4H)-benzopyranone 0.5 g and 3,4-dihydroxybenzaldehyde 0.42 g were added to a mixture of concentrated hydrochloric acid 25 ml and methanol 35 ml, the mixture was refluxed for 2.5 hours and cooled to room temperature, and water 250 ml was added. The mixture was allowed to stand for 18 hours and the precipitated crystals were filtered. The crystals were dried over phosphorous pentoxide for four hours under reduced pressure to obtain the desired compound 0.61 g.

FAB MASS (M+1); 285

$^1$H-NMR (ppm, in DMSO-$d_6$); 5.34 (2H, d, J=1.6 Hz), 6.29 (1H, d, J=2.1 Hz), 6.53 (1H, dd, J=8.6, 2.2 Hz), 6.74 (1H, dd, J=8.2, 1.8 Hz), 6.82 (2H, m), 7.51 (1H, s), 7.71 (1H, d, J=8.8 Hz), 9.19 (1H, s), 9.55 (1H, s), 10.57 (1H, s)

EXAMPLE 15

Synthesis of 7-hydroxy-3-piperonylidene-4(4H)-benzopyranone

After 7-hydroxy-4(4H)-benzopyranone 1.0 g and piperonal 1.0 g were added to a mixture of concentrated hydrochloric acid 50 ml and methanol 75 ml, the mixture was refluxed for two hours and cooled to room temperature, and water 200 ml was added. The mixture was allowed to stand for one hour and the precipitated crystals were filtered. The crystals were dried over phosphorous pentoxide for four hours under reduced pressure to obtain the desired compound 0.266 g.

FAB MASS (M+1); 297

$^1$H-NMR (ppm, in DMSO-$d_6$); 5.33 (2H, d, J=1.6 Hz), 6.09 (1H, s), 6.31 (1H, d, J=2.1 Hz), 6.53 (1H, dd, J=8.8, 2.5 Hz), 6.93 (1H, dd, J=7.9, 1.2 Hz), 7.02 (2H, m), 7.59 (1H, s), 7.72 (1H, d, J=8.8 Hz), 10.64 (1H, s)

EXAMPLE 16

Synthesis of 3-[(1,4-benzodioxane)-6-methylene]-7-hydroxy-4(4H)-benzopyranone

After 7-hydroxy-4(4H)-benzopyranone 1.0 g and 1,4-benzodioxane-6-carboxyaldehyde 1.2 g were added to a mixture of concentrated hydrochloric acid 50 ml and methanol 40 ml, the mixture was refluxed for 1.5 hours and cooled to room temperature, and the precipitated crystals were filtered. The crystals were dried over phosphorous pentoxide for four hours under reduced pressure to obtain the desired compound 1.066 g.

FAB MASS (M+1); 311

$^1$H-NMR (ppm, in DMSO-$d_6$); 4.29 (4H, m), 5.33 (2H, d, J=1.6 Hz), 6.31 (1H, d, J=2.1 Hz), 6.53 (1H, dd, J=8.8, 2.4 Hz), 6.89–6.96 (3H, m), 7.56 (1H, s), 7.72 (1H, d, J=8.5 Hz), 10.62 (1H, s)

EXAMPLE 17

Synthesis of 3-[(3,4-dimethoxyphenyl)methylene]-7-hydroxy-4(4H)-benzopyranone

After 7-hydroxy-4(4H)-benzopyranone 1.0 g and 3,4-dimethoxybenzaldehyde 1.22 g were added to a mixture of concentrated hydrochloric acid 50 ml and methanol 40 ml, the mixture was refluxed for 1.5 hours and cooled to room temperature, water 100 ml was added and the mixture was allowed to stand for 30 minutes. The precipitated crystals were filtered.

The crystals were dried over phosphorous pentoxide for seven hours under reduced pressure to obtain the desired compound 0.255 g.

FAB MASS (M+1); 313

$^1$H-NMR (ppm, in DMSO-$d_6$); 3.80 (3H, s), 3.81 (3H, s), 5.39 (2H, d), 6.32 (1H, d, J=2.1 Hz), 6.54 (1H, dd, J=8.8, 2.2 Hz), 6.97–7.05 (3H, m), 7.63 (1H, s), 7.73 (1H, d, J=8.8 Hz)

EXAMPLE 18

Synthesis of 3-[(3-ethoxy-4-methoxyphenyl)methylene]-7-hydroxy-4(4H)-benzopyranone After a saturated hydrogen chloride-methanol solution 15 ml was added to 7-hydroxy-4(4H)-benzopyranone 1.0 g and 3-ethoxy-4-methoxybenzaldehyde 1.30 g, the mixture was srtirred for 22.5 hours, water 100 ml was added, and the precipitated crystals were filtered. The crystals were added to methanol 30 ml of 55° C., and the mixture was filtered. The resulting crystals were dried over phosphorous pentoxide for four hours under reduced pressure to obtain the desired compound 0.415 g.

FAB MASS (M+1); 327

$^1$H-NMR (ppm, in DMSO-$d_6$); 1.33 (3H, t), 3.81 (3H, s), 4.05 (2H, q), 5.38 (2H, d), 6.31 (1H, d, J=2.5 Hz), 6.53 (1H, dd, J=8.5, 2.1 Hz), 6.96–7.05 (3H, m), 7.62 (1H, s), 7.73 (1H, d, J=8.5 Hz)

EXAMPLE 19

Synthesis of 3-[(3-methoxy-4-ethoxyphenyl)methylene]-7-hydroxy-4(4H)-benzopyranone After a saturated hydrogen chloride-methanol solution 20 ml was added to 7-hydroxy-4(4H)-benzopyranone 1.0 g and 3-methoxy-4-ethoxybenzaldehyde 1.30 g, the mixture was srtirred for 18 hours, water 100 ml was added, and the precipitated crystals were filtered. The crystals were added to methanol 100 ml of 55° C., and the mixture was stirred for 15 minutes and filtered. The resulting crystals were dried over phosphorous pentoxide for four hours under reduced pressure to obtain the desired compound 0.216 g.

FAB MASS (M+1); 327

$^1$H-NMR (ppm, in DMSO-$d_6$); 1.33 (3H, t), 3.80 (3H, s), 4.05 (2H, q), 5.38 (2H, d), 6.31 (1H, d, J=2.1 Hz), 6.53 (1H, dd, J=8.5, 2.1 Hz), 6.93–7.03 (3H, m), 7.63 (1H, s), 7.73 (1H, d, J=8.8 Hz)

EXAMPLE 20

Synthesis of 3-[(3,4-diethoxyphenyl)methylene]-7-hydroxy-4(4H)-benzopyranone

After a saturated hydrogen chloride-methanol solution 20 ml was added to 7-hydroxy-4(4H)-benzopyranone 1.0 g and 3,4-diethoxybenzaldehyde 1.58 ml, the mixture was srtirred for 72 hours, water 100 ml was added, and the precipitated crystals were filtered. The crystals were added to methanol 60 ml of 55° C., and the mixture was stirred for 15 minutes and filtered. The resulting crystals were dried over phosphorous pentoxide for four hours under reduced pressure to obtain the desired compound 0.762 g.

FAB MASS (M+1); 341

$^1$H-NMR (ppm, in DMSO-$d_6$); 1.33 (6H, t), 4.07 (4H, q), 5.37 (2H, d), 6.31 (1H, d, J=2.4 Hz), 6.53 (1H, dd, J=8.8, 2.4 Hz), 6.93–7.02 (3H, m), 7.62 (1H, s), 7.73 (1H, d, J=8.6 Hz)

EXAMPLE 21

Synthesis of 3-[(3-methyl-4-methoxyohenyl)methylene]-7-hydroxy-4(4H)-benzopyranone After a saturated hydrogen chloride-methanol solution 20 ml was added to 7-hydroxy-4(4H)-benzopyranone 1.0 g and 3-methyl-4-methoxybenzaldehyde 0.87 g, the mixture was srtirred for 72 hours, water 100 ml was added, and the precipitated crystals were filtered. The crystals were added to methanol 50 ml of 55° C., and the mixture was stirred for 15 minutes and filtered. The resulting crystals were dried over phosphorous pentoxide for four hours under reduced pressure to obtain the desired compound 0.447 g.

FAB MASS (M+1); 297

$^1$H-NMR (ppm, in DMSO-$d_6$); 2.17 (3H, s), 3.83 (3H, s), 5.35 (2H, d), 6.31 (1H, d, J=2.2 Hz), 6.53 (1H, dd, J=8.6, 2.2

Hz), 7.02 (1H, d, J=8.5 Hz), 7.24 (2H, m), 7.59 (1H, s), 7.73 (1H, d, J=8.6 Hz)

EXAMPLE 22

Synthesis of 2-methoxy[(3-methoxy-4-ethoxyphenyl) methylene]-6-methoxy-1-tetralone After 6-methoxy-1-tetralone 1.0 g and 3-methoxy-4-ethoxybenzaldehyde 1.27 g were added to a mixture of concentrated hydrochloric acid 60 ml and methanol 50 ml, the mixture was refluxed for 2.5 hours. The reaction mixture was cooled to room temperature, and ethyl acetate 100 ml was added. The ethyl acetate solution was washed with water 100 ml twice and saturated salt solution 100 ml twice. The ethyl acetate solution was dehydrated with magnesium sulfate, and concentrated to 20 ml at 40° C. under reduced pressure. The precipitated crystals were filtered. The crystals were dried over phosphorous pentoxide for four hours under reduced pressure to obtain the desired compound 0.89 g.

FAB MASS (M+1); 339

$^1$H-NMR (ppm, in CDCl$_3$); 1.46 (3H, t), 2.89 (2H, m), 3.10 (2H, m), 3.83 (3H, s), 3.86 (3H, s), 4.22 (2H, q, 4 Hz), 6.67 (1H, d, J=8.2 Hz), 6.83 (1H, dd, J=8.3, 1.9 Hz), 6.85 (1H, d, J=8.2 Hz), 6.65 (1H, d, J=1.8 Hz), 7.00 (1H, dd, J=8.5, 2.1 Hz), 7.65 (1H, s), 8.07 (1H, d, J=8.8 Hz)

in vitro 17β-HSD inhibition activity test

17β-HSD inhibition activity of the compounds obtained in Examples 1–22 (abbreviated as a test material hereinafter) was tested. Namely, each test material was dissolved in ethanol to obtain a solution of 260 nM of final concentration, placed in a test tube, and evaporated to dryness in nitrogen gas. To the material, a buffer solution of 10 mM phosphate 590 μl (pH 7.5) containing 100 mM potassium chloride, 1 mM ethylenediamine tetraacetic acid, 0.5 mM nicotinamide adenine dinucleotidephosphate of a reducing type (all compounds were available from Wako Junyaku Company) and 1 μM [4-$^{14}$C]estrone (NEN Research Products Company), and a microsome fraction 10 μl obtained from human placenta according to a method of E. A. Thompson et al (J. Biol. Chem., vol. 249, 5364–5372 (1974)) were added, and the mixture was reacted with shaking for 30 minutes at a temperature of 37° C. After the reaction, dichloromethane 2 ml was added at once. The mixture was thoroughly stirred, and centrifuged for five minutes at 3,000 rpm. The resulting lower layer (a dichloromethane layer) was removed to another test tube, and evaporated to dryness. To the tube, ethanol 100 μl containing estrone 20 μg and estradiol 20 μg was added, and 20 μl of the mixture was spotted on a TLC plate (silica gel 60 F$_{254}$, Merck Company). After the TLC plate was developed with benzene:acetone (4:1), spots corresponding to estrone and estradiol were cut off under ultraviolet light, liquid scintillation cocktail (Filter count (trademark); Hewlett Packard Company) was added to determine the amount of residual [4-$^{14}$C] estrone, and the amount of [4-$^{14}$C] estradiol produced by 17β-HSD enzyme activity by using a liquid scintillation counter. Further, as a control group, similar operation is conducted without adding the test materials. The 17β-HSD enzyme activity of the control group was determined as 0% of inhibition ratio, and the 17β-HSD enzyme inhibition ratio of the test materials were determined by percentage. The results are shown in FIGS. 1–3.

Industrial Applicability

From the above results, it is confirmed that the derivatives of the present invention (test materials) have excellent 17β-HSD inhibition activity. accordingly, from the present invention, new tetralone or benzopyranone derivatives and a method for producing the derivatives can be provided. The derivatives of the present invention have inhibition activity of 17β-HSD, and for the activity, these derivatives are useful for a therapeutic agent for preventing and/or treating androgen or estrogen dependent diseases, particularly, prostatic cancer, benign prostatic hyperplasia, virilism, mammary cancer, mastopathy, endometrial cancer, endometriosis, ovarian cancer and the like. Further, these compounds of the present invention can be used in a photoresist composition of positive type.

What is claimed is:

1. A tetralone or benzopyranone derivative represented by the following general formula (I):

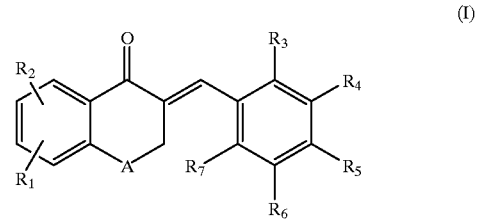

wherein R$_1$ represents a substituent substituted at the 6-position of said tetralone or the 7-position of said benzopyranone derivative selected from the group consisting of a hydroxy group, an alkyloxy group or an aralkyloxy group; R$_2$ is hydrogen; R$_3$–R$_7$ represent hydrogen, a hydroxy group, or a straight or branched alkyl, alkyloxy or aralkyloxy group having 1–6 carbon atoms, a halogen, an amino group or an alkylene dioxy group joined at R$_3$ and R$_4$, R$_4$ and R$_5$, R$_5$ and R$_6$, or R$_6$ and R$_7$; and A represents a methylene or oxygen, provided (i) when A is oxygen, R$_1$ is hydroxy, and R$_2$, R$_3$, R$_4$, R$_6$ and R$_7$ are hydrogen, then R$_5$ is not methoxy; and (ii) when A is methylene, R$_1$ is methoxy, and R$_2$, R$_3$ R$_4$, R$_6$ and R$_7$ are hydrogen, then R$_5$ is not methoxy or halogen.

2. A tetralone or benzopyranone derivative according to claim 1, wherein said derivative is a member selected from the group consisting of 2-[3,4-dihydroxyphenyl)methylene]-6-hydroxy-1-tetralone; 2-(phenylmethylene)-6-hydroxy-1-tetralone; 2-[(3-hydroxyphenyl)methylene]-6-hydroxy-1-tetralone; 2-[(4-hydroxyphenyl)methylene]-6-hydroxy-1-tetralone; 2-[(2-methoxyphenyl-4-carboxylic acid) methylene]-6-hydroxy-1-tetralone; 2-[(4-dimethylaminophenyl)methylene]-6-hydroxy-1-tetralone; 2[(3,4-dimethoxyphenyl)methylene]-6-hydroxy-1-tetralone; 2-[(3,5-dimethoxyphenyl)methylene]-6-hydroxy-1-tetralone; 2-[(4-bromophenyl)methylene]-6-hydroxy-1-tetralone; 2-[(4-chlorophenyl)methylene]-6-hydroxy-1-tetralone; 2-[(4-fluorophenyl)methylene]-6-hydroxy-1-tetralone; 6-hydroxy-2-piperonylidene-1-tetralone; 2-[(3,4-benzodioxane)-6-methylene]-6-hydroxy-1-tetralone; 2-[(3, 4-dihydroxyphenyl),methylene]-7-hydroxy-4(4H)-benzopyranone; 7-hydroxy-3-peperonylidene-4(4H)-benzopyranone; 3-[(1,4-benzodioxane)-6-methylene]-7-hydroxy -4(4H)-benzopyranone; 3-[(3,4-dimethoxyphenyl) methylene]-7-hydroxy-4(4H)-benzopyranone; 3-[(3-ethoxy-4-methoxyphenyl)methylene]-7-hydroxy-4(4H)-benzopyranone; 3-[(3-methoxy-4-ethoxyphenyl) methylene]-7-hydroxy-4(4H)-benzopyranone; 3-[(3,4-diethoxyphenyl)methylene]-7-hydroxy-4(4H)-benzopyranone; 3-[(3-methyl -4-methoxyphenyl) methylene]-7-hydroxy-4(4H)-benzopyranone; and 2-methoxy[(3-methoxy-4-ethoxyphenyl)methylene]-6-methoxy-1-tetralone.

3. A method for producing the tetralone or benzopyranone derivative claimed in claim 1, characterized in that it comprises dissolving a tetralone or benzopyranone compound represented by the following general formula (II) and a benzaldehyde compound represented by the following general formula (III) in an organic solvent, refluxing with heating under acidic conditions, and purifying the desired compound from the reaction mixture:

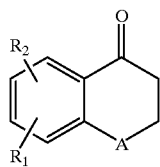

(II)

wherein $R_1$ represents a substituent substituted at the 6-position of said tetralone or the 7-position of said benzopyranone derivative selected from the group consisting of a hydroxy group, an alkyloxy group or an aralkyloxy group; $R_2$ is hydrogen; and A represents a methylene or oxygen;

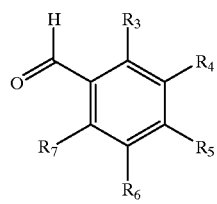

(III)

wherein $R_3$–$R_7$ represent hydrogen, a hydroxy group, or a straight or branched alkyl, alkyloxy or aralkyloxy group having 1–6 carbon atoms, a halogen, an amino group, or an alkylene dioxy group joined at $R_3$ and $R_4$, $R_4$ and $R_5$, $R_5$ and $R_6$, or $R_6$ and $R_7$.

4. A pharmaceutical composition comprising: a compound of the formula (I):

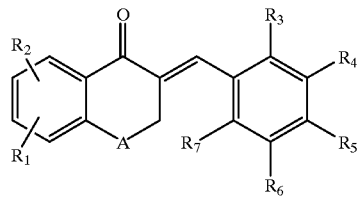

(I)

wherein $R_1$ represents a substituent substituted at the 6-position when A represents a methylene group or the 7-position when A represents an oxygen atom selected from the group consisting of a hydroxy group, an alkyloxy group or an aralkyloxy group; $R_2$ is hydrogen; $R_3$–$R_7$ represent hydrogen, a hydroxy group, or a straight or branched alkyloxy or aralkyloxy group having 1–6 carbon atoms, a halogen, an amino group or an alkylene dioxy group joined at $R_3$ and $R_4$, $R_4$ and $R_5$, $R_5$ and $R_6$, or $R_6$ and $R_7$; and A represents a methylene or oxygen; and a pharmaceutically acceptable carrier.

5. A pharmaceutical composition according to claim 4, wherein said compound is a member selected from the group consisting of 2-[3,4-dihydroxyphenyl)methylene]-6-hydroxy-1-tetralone; 2-(phenylmethylene)-6-hydroxy-1-tetralone; 2-[(3-hydroxyphenyl)methylene]-6-hydroxy-1-tetralone; 2-[(4-hydroxyphenyl)methylene]-6-hydroxy-1-tetralone; 2-[(2-methoxyphenyl-4-carboxylic acid)methylene]-6-hydroxy-1-tetralone; 2-[(4-dimethylaminophenyl)methylene]-6-hydroxy-1-tetralone; 2[(3,4-dimethoxyphenyl)methylene]-6-hydroxy-1-tetralone; 2-[(3,5-dimethoxyphenyl)methylene]-6-hydroxy-1-tetralone; 2-[(4-bromophenyl)methylene]-6-hydroxy-1-tetralone; 2-[(4-chlorophenyl)methylene]-6-hydroxy-1-tetralone; 2-[(4-fluorophenyl)methylene]-6-hydroxy-1-tetralone; 6-hydroxy-2-piperonylidene-1-tetralone; 2-[(3,4-benzodioxane)-6-methylene]-6-hydroxy-1-tetralone; 2-[(3,4-dihydroxyphenyl),methylene]-7-hydroxy-4(4H)-benzopyranone; 7-hydroxy-3-peperonylidene-4(4H)-benzopyranone; 3-[(1,4-benzodioxane)-6-methylene]-7-hydroxy-4(4H)-benzopyranone; 3-[(3,4-dimethoxyphenyl)methylene]-7-hydroxy-4(4H)-benzopyranone; 3-[(3-ethoxy-4-methoxyphenyl)methylene]-7-hydroxy-4(4H)-benzopyranone; 3-[(3-methoxy-4-ethoxyphenyl)methylene]-7-hydroxy-4(4H)-benzopyranone; 3-[(3,4-diethoxyphenyl)methylene]-7-hydroxy-4(4H)-benzopyranone; 3-[(3-methyl-4-methoxyphenyl)methylene]-7-hydroxy-4(4H)-benzopyranone; and 2-methoxy[(3-methoxy-4-ethoxyphenyl)methylene]-6-methoxy-1-tetralone.

6. A method for treating a hormone dependent disease in a mammal, said method comprising: administering a compound of the formula

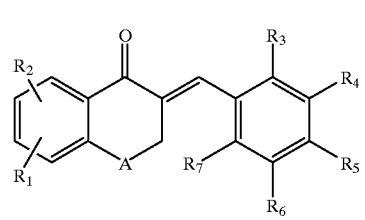

(I)

wherein $R_1$ represents a substituent substituted at the 6-position of said tetralone or the 7-position of said benzopyranone derivative selected from the group consisting of a hydroxy group, an alkyloxy group or an aralkyloxy group; $R_2$ is hydrogen; $R_3$–$R_7$ represent hydrogen, a hydroxy group, or a straight or branched alkyl, alkyloxy or aralkyloxy group having 1–6 carbon atoms, a halogen, an amino group or an alkylene dioxy group joined at $R_3$ and $R_4$, $R_4$ and $R_5$, $R_5$ and $R_6$, or $R_6$ and $R_7$; and A represents a methylene or oxygen; and thereby treating said hormone depend disease.

7. A method according to claim 6, wherein said compound is a member selected from the group consisting of 2-[3,4-dihydroxyphenyl)methylene]-6-hydroxy-1-tetralone; 2-(phenylmethylene)-6-hydroxy-1-tetralone; 2-[(3-hydroxyphenyl)methylene]-6-hydroxy-1-tetralone; 2-[(4-hydroxyphenyl)methylene]-6-hydroxy-1-tetralone; 2-[(2-methoxyphenyl-4-carboxylic acid)methylene]-6-hydroxy-1-tetralone; 2-[(4-dimethylaminophenyl)methylene]-6-hydroxy-1-tetralone; 2-[(3,4-dimethoxyphenyl)methylene]-6-hydroxy-1-tetralone; 2-[(3,5-dimethoxyphenyl)methylene]-6-hydroxy-1-tetralone; 2-[(4-bromophenyl)methylene]-6-hydroxy-1-tetralone; 2-[(4-chlorophenyl)methylene]-6-hydroxy-1-tetralone; 2-[(4-fluorophenyl)methylene]-6-hydroxy-1-tetralone; 6-hydroxy-2-piperonylidene-1-tetralone; 2-[(3,4-benzodioxane)-6- methylene]-6-hydroxy-1-tetralone; 2-[(3,4-dihydroxyphenyl),methylene]-7-hydroxy-4(4H)-benzopyranone; 7-hydroxy-3-peperonylidene-4(4H)-benzopyranone; 3-[(1,4-benzodioxane)-6-methylene]-7-hydroxy-4(4H)-benzopyranone; 3-[(3,4-dimethoxyphenyl) methylene]-7-hydroxy-4(4H)-benzopyranone; 3-[(3-methoxy-4-methoxyphenyl)methylene]-7-hydroxy-4(4H)-benzopyranone; 3-[(3-methoxy-4-ethoxyphenyl) methylene]-7-hydroxy-4(4H)-benzopyranone; 3-[(3,4-diethoxyphenyl)methylene]-7-hydroxy-4(4H)-benzopyranone; 3-[(3-methyl-4-methoxyphenyl) methylene]-7-hydroxy-4(4H)-benzopyranone; and 2-methoxy[(3-methoxy-4-ethoxyphenyl)methylene]-6-methoxy-1-tetralone.

8. A method according to claim 6, wherein said disease is a member selected from the group consisting of prostate cancer, benign prostatic hyperplasia, virilism, mammary cancer, mastopathy, endometrial cancer, endometriosis and ovarian cancer.

* * * * *